US009686395B2

(12) United States Patent
Erickson et al.

(10) Patent No.: US 9,686,395 B2
(45) Date of Patent: Jun. 20, 2017

(54) APPARATUS AND METHOD FOR POINT-OF-COLLECTION MEASUREMENT OF A BIOMOLECULAR REACTION

(71) Applicant: CORNELL UNIVERSITY, Ithaca, NY (US)

(72) Inventors: David Erickson, Ithaca, NY (US); Matthew Mancuso, Bohemia, NY (US); Seoho Lee, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 155 days.

(21) Appl. No.: 14/427,049

(22) PCT Filed: Sep. 6, 2013

(86) PCT No.: PCT/US2013/058422
§ 371 (c)(1),
(2) Date: Mar. 10, 2015

(87) PCT Pub. No.: WO2014/042979
PCT Pub. Date: Mar. 20, 2014

(65) Prior Publication Data
US 2015/0244852 A1     Aug. 27, 2015

Related U.S. Application Data

(60) Provisional application No. 61/699,486, filed on Sep. 11, 2012.

(51) Int. Cl.
*H04M 1/725*     (2006.01)
*G01N 21/31*     (2006.01)
(Continued)

(52) U.S. Cl.
CPC ........ *H04M 1/72527* (2013.01); *G01N 21/31* (2013.01); *G01N 21/78* (2013.01);
(Continued)

(58) Field of Classification Search
CPC ...... B01L 3/502715; G01N 2015/0038; G01N 2035/00881; G01N 21/31; G01N 21/78;
(Continued)

(56) References Cited

U.S. PATENT DOCUMENTS 8,697,435 B2 *   4/2014   Heil ................. G01N 33/54326
    422/414
2005/0257627 A1 *   11/2005   Kitamura ................ G01L 5/166
    73/862.381
(Continued)

FOREIGN PATENT DOCUMENTS

KR    1020120034485 A    4/2012
KR    1020120095754 A    8/2012
(Continued)

OTHER PUBLICATIONS

International Search Report and Written Opinion Form PCT/ISA/220, International Application No. PCT/US2013/058422, pp. 1-12, International Filing Date : Sep. 6, 2013.
(Continued)

*Primary Examiner* — Jennifer Wecker
(74) *Attorney, Agent, or Firm* — Bond, Schoeneck & King, PLLC; William Greener; Erin Phillips (57) ABSTRACT

A system, methods, and apparatus for biomolecular measurements, monitoring, and tracking uses a smartphone-based system. A biological sample, including, but not limited to blood, saliva, biopsy, or sweat, is collected on a modular diagnostic test platform, which is then inserted into a smartphone accessory. Optical, electrical, mechanical, or other means are used to transduce a biomolecular binding event, including antibody, aptamer, enzymatic, base-pair matching, or other biological recognition reaction and communicate the results with the smartphone. Some specific examples of targets include 25-hydroxyvitamin D, folic acid, DNA, or proteins from infectious agents, and zinc. The
(Continued)

result can then be presented quantitatively or turned into a more consumer-friendly measurement (positive, negative, above average, etc.), displayed to the user, stored for later comparison, and communicated to a central hub location where medical professionals can provide additional review. Additionally, social media integration can allow for device results to be broadcast to specific audiences, to compare healthy living with friends, to compete in health based games, create mappings, and other applications.

19 Claims, 9 Drawing Sheets

(51) Int. Cl.
| | | |
|---|---|---|
| *G01N 21/17* | (2006.01) | |
| *G01N 21/78* | (2006.01) | |
| *G06Q 50/22* | (2012.01) | |
| *G01N 33/48* | (2006.01) | |
| *G01N 33/487* | (2006.01) | |
| *G06F 19/00* | (2011.01) | |
| *G01N 15/00* | (2006.01) | |
| *B01L 3/00* | (2006.01) | |
| *G01N 35/00* | (2006.01) | |

(52) U.S. Cl.
 CPC ........ *G06F 19/3406* (2013.01); *G06F 19/366* (2013.01); *G06Q 50/22* (2013.01); *B01L 3/502715* (2013.01); *G01N 33/48792* (2013.01); *G01N 2015/0038* (2013.01); *G01N 2035/00881* (2013.01); *G01N 2201/062* (2013.01); *G01N 2201/12* (2013.01); *G06F 19/3418* (2013.01)

(58) Field of Classification Search
 CPC .......... G01N 2201/062; G01N 2201/12; G06F 19/3406; G06F 19/3418; G06F 19/366; G06Q 50/22; H04M 1/72527
 See application file for complete search history.

(56) References Cited

U.S. PATENT DOCUMENTS

| | | | | |
|---|---|---|---|---|
| 2006/0222567 | A1* | 10/2006 | Kloepfer | ................ G01N 21/78 422/68.1 |
| 2010/0220328 | A1* | 9/2010 | Isaka | ................... G01N 21/554 356/445 |
| 2011/0063433 | A1* | 3/2011 | Thonhauser | ......... G01N 21/251 348/135 |
| 2011/0165688 | A1* | 7/2011 | Dupoteau | ............ A61B 5/1172 436/55 |
| 2011/0253224 | A1* | 10/2011 | Linder | .................. B01L 3/5027 137/2 |
| 2012/0123686 | A1* | 5/2012 | Xiang | ................. G06F 19/3406 702/19 |
| 2012/0225491 | A1 | 9/2012 | Ram et al. | |
| 2012/0315665 | A1* | 12/2012 | Eckhardt | ............. G01N 33/558 435/34 |

FOREIGN PATENT DOCUMENTS

| | | |
|---|---|---|
| WO | 2005074161 A1 | 11/2005 |
| WO | 2012010811 A1 | 1/2012 |
| WO | 2013119266 | 8/2013 |

OTHER PUBLICATIONS

Stedtfeld, Robert D., et al, "Gene-Z: a device for point of care genetic testing using a smartphone", Lab Chip, vol. 12, No. 8, 2012, pp. 1454-1462.

Emmadi, Rajyasree, et al., "Molecular Methods and Platforms for Infectious Diseases Testing", Journal of Molecular Diagnostics, vol. 13, No. 6, Nov. 2011, pp. 583-604.

Mudanyali, Onur, et al., "Integraded rapid-daignostic-test reader platform on a cellphone", Lab Chip, vol. 12, No. 15, 2012, pp. 2678-2686.

\* cited by examiner

APPARATUS AND METHOD FOR POINT-OF-COLLECTION MEASUREMENT OF A BIOMOLECULAR REACTION

RELATED APPLICATION DATA

The instant application claims priority to U.S. provisional Application Ser. No. 61/699,486 filed on Sep. 11, 2012, the subject matter of which is incorporated by reference in its entirety.

TECHNICAL FIELD

Embodiments of the present invention relate generally to the field of biomolecular diagnostics and, more particularly to portable, point of collection diagnostic systems, methods, and components for biomolecular reaction measurements, monitoring, tracking, and reporting, including social media applications.

BACKGROUND

Modern efforts in medicine and healthy living involve the delivery of personalized care and management to the patient. Due to the high variance inherent in biology, including in diagnostic criteria, treatment, and disease management, often the best solution for one patient is far from ideal for another. Before optimal treatment and healthy living for an individual can be prescribed by medical providers, the first step is collecting information about them; however, to date much of this data collection relies on questionnaires and surveys, diagnostic tests being prohibitively expensive, especially for groups that are not an immediate risk. These sorts of human input are often highly variable as they rely on a patient's ability to recall their past behavior as well as their integrity and embarrassment in admitting certain actions associated with (supposed) unhealthy living.

The cost and accessibility of traditional medical diagnostic instruments can and needs to be improved. Currently, diagnosis of disease can take days to weeks while results are sent off to a laboratory, and many diseases still cannot accurately be detected. Devices capable of quickly and accurately diagnosing multiple conditions could be applied to situations ranging from nutrition and vitamin management in first-world locales to antibiotic and vaccine triage in third-world villages. If created and packaged correctly, such devices could ease the burden on gateway physicians, provide impoverished countries with now inaccessible diagnostic capabilities, protect combatants from biological warfare agents, and increase health care access to the average person.

One implementation of these state-of-the-art diagnostics is as smartphone and/or tablet (i.e., portable computing) accessories where the computational power, read-out, data storage, and connectivity are provided by an existing device. The smartphone has penetrated nearly all aspects of our lives, affecting how we consume media including news and entertainment, how we track our finances and pay for goods and services, and how we monitor our health and fitness. However, for all of the benefits smartphones have provided, there is still little or no direct connection between smartphones and in vivo biochemistry. By enabling a direct link between a smartphone and small molecule detection, monitoring, and tracking, a number of new benefits could be realized in the fields of medicine and healthy living, including, e.g., simple diagnosis of disease and nutrient deficiencies; monitoring and tracking of existing conditions; and social media-enabled healthy living updates, competition, game playing, and mapping.

Suboptimal nutrition is one of the most acute problems facing the developed and developing world today. Worldwide, there are more disability-adjusted life years lost to malnutrition than any other medical condition; it is reported that over 1,000,000 people die every year from vitamin A and zinc deficiencies, and 30% of all cancers are related to poor diet (by comparison genetics and obesity account for only 5% and 10% of all cancers respectively). Optimal pre-natal maternal folic acid levels are well co-related with a reduction in neural tube defects and evidence suggests that fetal brain development is enhanced by docosahexaenoic acid (DHA) intake. Micronutrient (i.e., vitamins and minerals) deficiencies have been tied to dozens of different health conditions including anemia, rickets, scurvy, cardiovascular disease, and cancer. Additionally, recent work has linked vitamin deficiencies to obesity, one of the major challenges facing the current generation.

The Copenhagen Consensus has identified tackling vitamin and micronutrient deficiencies as the most cost-effective intervention to further global development and progress in published reports since 2004. Domestically, the Institute of Medicine has concluded half of older adults in the United States who had hip fractures had serum levels of 25(OH)D less than 12 ng/mL; (25-hydroxyvitamin D [25(OH)D] is considered to be the best indicator of vitamin D; and, that levels below 20 ng/mL are inadequate for bone and overall health. The vast majority of vitamin and micronutrient analysis is done through blood collection via venipuncture, which is then sent away to a centralized laboratory. This analysis is slow, expensive, requires trained personnel, and is not widely available, particularly in resource-limited settings where micronutrient deficiency is most harmful. A combined HPLC-MS method is considered the industry standard for vitamin D testing, however ELISA kits and similar immunoassays are comparable in terms of sensitivity and accuracy, while being better suited for adaption to home use. Since micronutrient deficiencies are not often clinically obvious, these tests are typically done at the insistence of the patient. The fact that so many Americans are vitamin deficient testifies to the fact that the current methodologies are not working.

Salivary cortisol is a routinely used biomarker of stress and related psychological diseases. Commonly, cortisol is elevated in patients who experience a sudden stressor and returns to normal after a period of time whose length is dependent on the strength of the stressor. In patients with chronic stress disorders, such as PTSD, it has been difficult to co-relate absolute levels of cortisol at any given time with the diagnosis of a disorder due to the large number of confounders. A better approach would be to track cortisol, and other biomarkers, over time to look for trends that could be indicative of the onset psychological disease.

Every year hundreds of millions of people suffer from infectious diseases including respiratory infections, HIV/AIDS, diarrheal diseases, tuberculosis, and malaria. The agents that cause these diseases, including bacteria, viruses, fungi, etc., are often easily manageable with proper identification yet routinely go undetected because of the costs and difficulties associated with diagnostic technology. In some cases, such as tuberculosis, identifying the disease rapidly and on location can allow for preventative measures prohibiting the disease from spreading further. In other cases, such as HIV, keeping an acute-eye on antibody levels is critical in tracking the progress of the disease.

Kaposi's sarcoma (KS) is an opportunistic infectious cancer that first became widely known during the acquired immunodeficiency syndrome (AIDS) epidemic of the 1980s. During this time period, the appearance of symptoms of KS, red lesions on the skin, became signs that an individual was infected with human immunodeficiency virus (HIV) and KS itself became known as an AIDS-defining illness. As the battle against AIDs waged on, the introduction of highly active anti-retroviral therapy (HAART) helped reduce KS incidence. Years later, however, HIV infected individuals still contract KS at a higher occurrence than when compared to the pre-AIDS era. Today, KS is the fourth leading cancer in sub-Saharan Africa, and in some countries, such as Uganda, is the most prevalent cancer in men. The root cause of KS is Human herpes virus 8 (HHV-8), more commonly referred to as Kaposi's sarcoma associated herpes virus (KSHV). While the virus is often asymptomatic in healthy individuals, a number of populations, including those immune-compromised by HIV, are vulnerable to its symptoms. The virus is commonly believed to be transmitted through saliva and in some regions rapidly spreads, beginning in childhood affecting large portions of the population, reaching seroprevalence of over 50%. Like other herpes viruses, KSHV can establish a latent infection and remains without causing any disease for the remaining life in most infected hosts, being necessary but not sufficient of KS development.

In the developed world, medical professionals diagnose KS with sufficient accuracy. If typical hematoxylin and eosin (H&E) staining are applied to a KS biopsy section a number of unique features can be observed, including many and large vascular spaces as well as high numbers of spindle cells thought to be of lymphatic endothelial origin. However, due to the existence of similarly presenting diseases, such as bacillary angiomatosis (BA), identification of these features is not sufficient for diagnosis of KS. In modern hospitals this is solved through immunohistochemistry staining for protein markers of KSHV, or through application of PCR for KSHV sequences. However, neither of these techniques is readily adaptable for use in the developing world where KS is most prevalent.

Finding a solution to the aforementioned types of challenges and problems directly motivated the development of lab-on-a-chip based point-of-care diagnostics, beginning some 15 years ago. The technical vision behind these kinds of systems comprised two parts: a consumable "chip" that contains microfluidics and a biosensor, and a "reader" instrument that interprets the signal from the chip and provides results to the operator. Since this vision was first put forward, the technology has advanced at an incredible rate to the point where we now have devices that can operate over a million microfluidic valves in parallel, portable PCR machines for pathogen detection, nanosensors that can detect a handful of molecules, and numerous other systems. These developments have significantly reduced the size of the sample required to perform a blood analysis.

To date, little of this visionary technology has transitioned to personalized nutritional and vitamin analysis, for example. There are two reasons for this: first is the difficulty in obtaining quantitative results with a simple one-off test. The majority of commercially available point-of-use tests for the consumer market are based on the lateral flow principle. Unfortunately, these types of tests are only able to provide non-quantitative information and are only useful when the desired result is binary (e.g. pregnant/not-pregnant). Obtaining quantitative results requires complex sensors and sample handling techniques that typically must be interpreted and displayed by a reusable reader. This leads to the second challenge: In the marketplace, the reader/consumable model (e.g., the razor/razor blades) has proven successful only where the user makes numerous measurements over the course of a day or week (e.g., blood glucose monitoring). When measurements are made sporadically or with much lower frequency (as with vitamins) the cost of purchasing a reader system is prohibitively high, even if the consumable can be made relatively inexpensive.

The extreme societal penetration of smartphones holds the potential to alter this predicament. It is predicted that by 2016 there will be 250 million smartphones in use in the US. A good portion of the complexity required to make and interpret a quantitative in-vitro measurement is already embedded in smartphones, resulting in a paradigm shift in the "razor and blades" model. Put simply, most consumers now already own the expensive part, the "Razor," in the form of a smartphone; all one needs then is the blades.

A number of systems have been developed. Examples include fitness monitoring, vaccine logs, sleep monitoring apps, and skin cancer diagnostics. Smartphones have been used to collect heart rate, blood pressure, and blood oxygen saturation. In 2011, smartphone-based healthcare was worth $1.3 billion, up nearly twice its 2010 value. Importantly however, all these existing commercial smartphone based systems rely on user input or physical measurements that are generally non-specific to a particular pathology.

The inventors have recognized that expansion beyond these coarse measurements requires molecular analysis of bodily fluids like sweat, saliva, urine and blood, all of which contain a much deeper wealth of physiological information. The inventors have also recognized a need for mobile, point-of-collection devices and methods that address all of the challenges outlined above. Most importantly, the inventors have recognized the benefits and advantages of a smartphone-type system, components thereof, associated methods, and applications for quantitative bimolecular detection assays, embodiments of which will be described in detail below. Regardless of the disease, nutritional deficiency, or other foci of the measurement, rapid, point-of-collection, smartphone-based detection could provide enormous benefits in terms of the amount of information that could be provided to medical personnel. The temporal resolution and time-charted measurements provided by smartphone diagnostics could be critical in treating individual patients and providing needed personalized care. The geographic information and connectivity of smartphones could be key in tracking diseases or other agents spreading through populations. By leveraging the processing power, display, and other components of a smartphone-type system, point-of-care diagnostics could be made considerably less expensive than modalities currently available.

SUMMARY

As used herein, the term 'smartphone' or 'smartphone-type device/system' means a mobile apparatus that is capable of running a programmed application suitable for executing the embodied functionality. While suitable traditional smartphone or smartphone-type devices may include, e.g., products such as the iPhone (Apple, Inc.) or Android (Google Inc.)-based smartphones and tablet computers, a smartphone or smartphone-type device (e.g., Apple iPad) as discussed and embodied herein need not include a telephone, per se, and may or may not include a built-in light source (e.g., flash) and/or camera/CCD and, therefore, may include tablets or other devices having size and weight characteristics similar to, or smaller/lighter than, conventional smartphones or smartphone-type devices. Thus a 'laptop' computer would not necessarily be covered under the definitional use of the term 'smartphone;' nor would a computing device that could be made 'portable' or 'mobile' by an accompanying apparatus that might give it portability or mobility. For the sake of conciseness, the term 'smartphone' will be used herein (including the claims) to mean smartphones or smartphone-type devices as discussed within the paragraph above.

The term 'rapid' as used herein (and in the claims) to modify the phrase 'point-of-collection, quantitative target measurement of a biomolecular reaction in a collected sample' is defined to mean 'essentially in real time' (e.g., seconds, minutes).

The term 'point-of-collection' as used herein (and in the claims) to modify the phrase 'quantitative target measurement of a biomolecular reaction in a collected sample' is defined to mean making a rapid target measurement at the time a sample is collected on a modular diagnostic test platform in possession of the user and inserted into the possessed smartphone accessory, not at a later time, for example, after a sample has been collected and sent to a laboratory.

An embodiment of the invention is a method for measuring a target of a biomolecular reaction in a biological sample using a smartphone. Illustrative steps include: collecting a sample on a diagnostic test platform; recognizing the sample; communicating sample information (signal transduction) from the diagnostic test platform to a smartphone sample analyzer component (smartphone reader/accessory); and signal processing the sample for analysis. Optional additional steps include interpretation and/or display of the assay results on the smartphone and/or using a smart phone and smart phone application for measurement, logging, tracking, and sharing of measurement information enabled by smartphone connectivity and social media. The embodied method may be characterized by the following illustrative, exemplary, non-limiting aspects:

sample collection through a finger prick to collect a droplet of blood;

sample collection through collection of saliva via ejection or cheek swab;

sample collection via urine, sweat, tear, or other bodily fluid collection;

sample collection through collection and processing of a solid sample including a biopsy or DNA from a biopsy;

sample collection through collection and processing of gas samples by collection of respiratory output;

sample recognition through antibody-antigen recognition;

sample recognition through DNA base pair recognition;

sample recognition through aptamer-target recognition;

sample recognition through enzymatic recognition;

signal transduction through optical, electrical, mechanical, or other means, including optical, electrical, or mechanical signal amplification based on resonance or other means taking place between a disposable test platform and a reader accessory;

signal transduction using surface enhanced Raman spectroscopy to obtain a "fingerprint" of specific biomolecules;

signal transduction via an absorption measurement at specific wavelengths, wherein biomolecular recognition is turned into a change in these wavelengths via gold nanoparticle and/or other nanoparticle-based assays;

measurement, logging, tracking, and sharing enabled by smartphone connectivity and social media;

detection via gold nanoparticles;

detection on a surface;

detection in a solution;

detection via comparing (ratiometric) an absorbance of a test assay to that of a control;

providing a quantitative target measurement;

where the detected targets are vitamins, minerals, other micronutrients, pH, hormones, viruses, bacteria, or factors associated therewith (e.g., vitamin/nutrient deficiencies; stress associated with cortisol levels; sodium concentration, others);

where the target detected is vitamin D, or any of its down-stream metabolites, including 25-hydroxyvitamin D, 1,25-dihydroxyvitamin D, or 25-hydroxycholecalciferol;

where the targets detected are pathogens, pathogen proteins, pathogen nucleic acids, or other pathogen biomolecules;

where the biomolecules detected is KSHV DNA.

An embodiment of the invention is a smartphone-based system capable of performing a biomolecular assay on an analyte. The smartphone-based system includes a smartphone, a smartphone application, and a smartphone accessory. According to various non-limiting, exemplary aspects:

wherein the smartphone-based system further comprises a modular, diagnostic test platform;

wherein the smartphone accessory includes a magnetic latch for removeably holding the modular diagnostic test platform;

wherein an LED light source is disposed directly across from a photodiode optical sensor, both of which are disposed behind respective pinhole apertures, in the case;

wherein the modular diagnostic test platform is a disposable test strip;

wherein the modular diagnostic test platform is a reusable component;

wherein the modular diagnostic test platform has a collapsible microchannel characterized by an aspect ratio wherein the microchannel is collapsible into a nanochannel;

wherein the modular, diagnostic test platform includes a sample collection region, a biomolecular reaction region, and a control reaction region;

wherein the modular diagnostic test platform includes a plurality of functionalized nanoparticles;

wherein the functionalized nanoparticles are functionalized with single-ended strands of DNA;

wherein the functionalized nanoparticles are coated with an oligonucleotide;

wherein the functionalized nanoparticles are functionalized with hydroxyvitamin D antibodies;

wherein the functionalized nanoparticles are functionalized with anti-hydroxyvitamin D antibodies;

wherein the modular diagnostic test platform includes at least two groups of functionalized gold nanoparticles which are each coated with a different oligonucleotide;

wherein the smartphone-based system is capable of performing a quantitative biomolecular assay on an analyte;

the smartphone application is configured to allow the smartphone to supply power for operation of the smartphone accessory;

the smartphone application is configured to provide email functionality;

the smartphone application is configured to store results on an Internet or cloud-based file storage and synchronization platform;

storing the results as text files;

storing the results on a Google Drive account;

the smartphone application is configured to create keyhole mark-up language files (KML files) that can be opened in Google Maps, Google Earth, or other geographic applications;

the smartphone accessory (reader) is connectable to a smartphone, wherein the smartphone accessory includes a case or housing;

wherein the smartphone accessory includes a smartphone connector;

wherein the smartphone connector is a μUSB connector;

wherein the smartphone accessory is connectable to a smartphone via a Bluetooth platform, a USB-type accessory, Wi-Fi, and a smartphone input port;

wherein the smartphone accessory includes a microcontroller;

wherein the smartphone accessory includes an optical sensor;

wherein the smartphone accessory includes a light source;

wherein the light source is a LED;

wherein the light source is a laser;

wherein the light source has a wavelength corresponding to a resonant absorbance peak of a gold nanoparticle (GNP);

wherein the light source has a wavelength centered around 520 nm;

wherein the smartphone accessory includes a spectrometer;

wherein the smartphone accessory includes a Raman detector.

An embodiment of the invention is a method that enables a rapid, point-of-collection, quantitative target measurement of a biomolecular reaction in a collected sample. The method includes the steps of providing a modular, diagnostic test platform that includes a sample collection region, a biomolecular reaction region, and a control reaction region; collecting a sample at the sample collection region; providing a smartphone and a smartphone accessory, wherein the smartphone is programmed with a software application that operatively couples the smartphone and the smartphone accessory, further wherein the smartphone accessory is one of operatively connectable to and operatively connected to the smartphone, further wherein the smartphone accessory is adapted to removeably retain the modular, diagnostic test platform including the collected sample, further wherein the smartphone accessory provides an ambient light-free environment for at least the biomolecular reaction region and the control region of the diagnostic test platform including the collected sample at least during a reaction measurement phase of the method, further wherein at least one of the smartphone and the smartphone accessory includes a light source having an emission that can illuminate at least the biomolecular reaction region and the control region of the diagnostic test platform; instructing the software application to activate the light source; making a ratiometric measurement of a biomolecular reaction in the biomolecular reaction region and a biomolecular reaction in the control reaction region; and displaying on the smartphone or the smartphone accessory a quantitative target measurement of the biomolecular reaction in the collected sample. According to various non-limiting, exemplary aspects, the method may include the following steps, features, components and/or characteristics:

wherein the biomolecular reaction region and the control reaction region each include a plurality of functionalized nanoparticles;

wherein the biomolecular reaction region and the control reaction region are in the form of microfluidic channels;

further comprising making the ratiometric measurement of the biomolecular reaction in the biomolecular reaction region and the biomolecular reaction in the control reaction region in parallel;

wherein the biomolecular reaction region and the control reaction region are in the form of serially disposed sub-regions on the diagnostic test platform;

wherein the biomolecular reaction region is disposed upstream of the control reaction region;

wherein the diagnostic test platform is a single-use, disposable component;

wherein the smartphone accessory further comprises a microcontroller operatively coupled to the software application, the light source, and a photodetector, wherein the light source emission is at a wavelength that corresponds to a resonant absorbance peak of the pluralities of the functionalized nanoparticles.

An embodiment of the invention is a diagnostic test platform. The diagnostic test platform includes a sample collection region, a biomolecular reaction region, and a control reaction region. According to various non-limiting, exemplary aspects, the diagnostic test platform may include the following, features, components and/or characteristics:

the biomolecular reaction region and the control reaction region each include a plurality of functionalized nanoparticles;

the biomolecular reaction region and the control reaction region are in the form of microfluidic channels;

wherein the microfluidic channels are collapsible into nanofluidic geometries;

wherein the biomolecular reaction region and the control reaction region are in the form of serially disposed sub-regions on the diagnostic test platform;

wherein the biomolecular reaction region is disposed upstream of the control reaction region;

wherein the diagnostic test platform is a single-use, disposable component.

Additional features and advantages of the invention will be set forth in the detailed description to follow, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and together with the description serve to explain the principles and operation of the invention.

BRIEF DESCRIPTION OF THE DRAWINGS

The present invention will be more fully understood and appreciated by reading the following Detailed Description in conjunction with the accompanying drawings, in which:

FIGS. 5(*a, b*) show a smartphone accessory according to an alternative exemplary aspect of the invention;

DETAILED DESCRIPTION OF NON-LIMITING, EXEMPLARY EMBODIMENTS OF THE INVENTION

Figure 1:
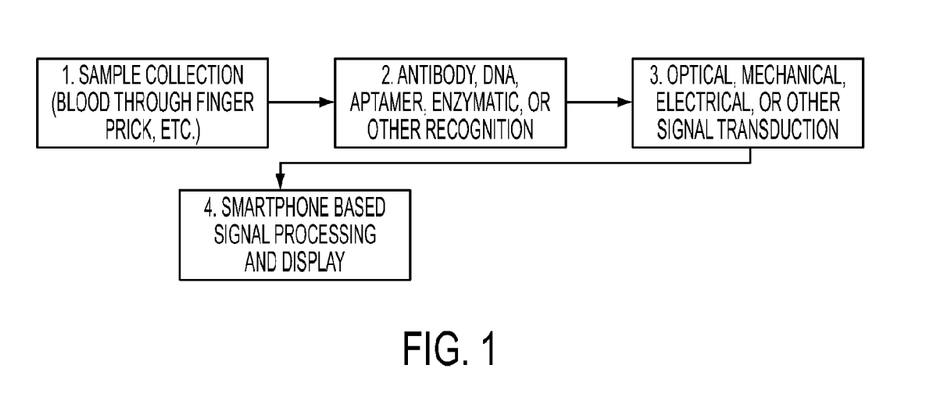
FIG. 1 is a high-level flow chart expressing the steps of a method for measuring a target of a biomolecular reaction in a biological sample using a smartphone, according to an embodiment of the invention.

An exemplary embodiment of the invention is a method for rapidly obtaining and presenting (i.e., displaying or communicating out) a quantitative target measurement of a biomolecular reaction in a collected biological sample at the time (and location) of the sample collection event using a specially adapted (embodied) smartphone system. FIG. 1 shows, at a high level, the method steps involved in making the aforementioned target measurement using a smartphone system as depicted in FIGS. 2-4, and, alternatively, FIG. 6, which method and apparatus will be described in greater detail as follows.

Figure 2:
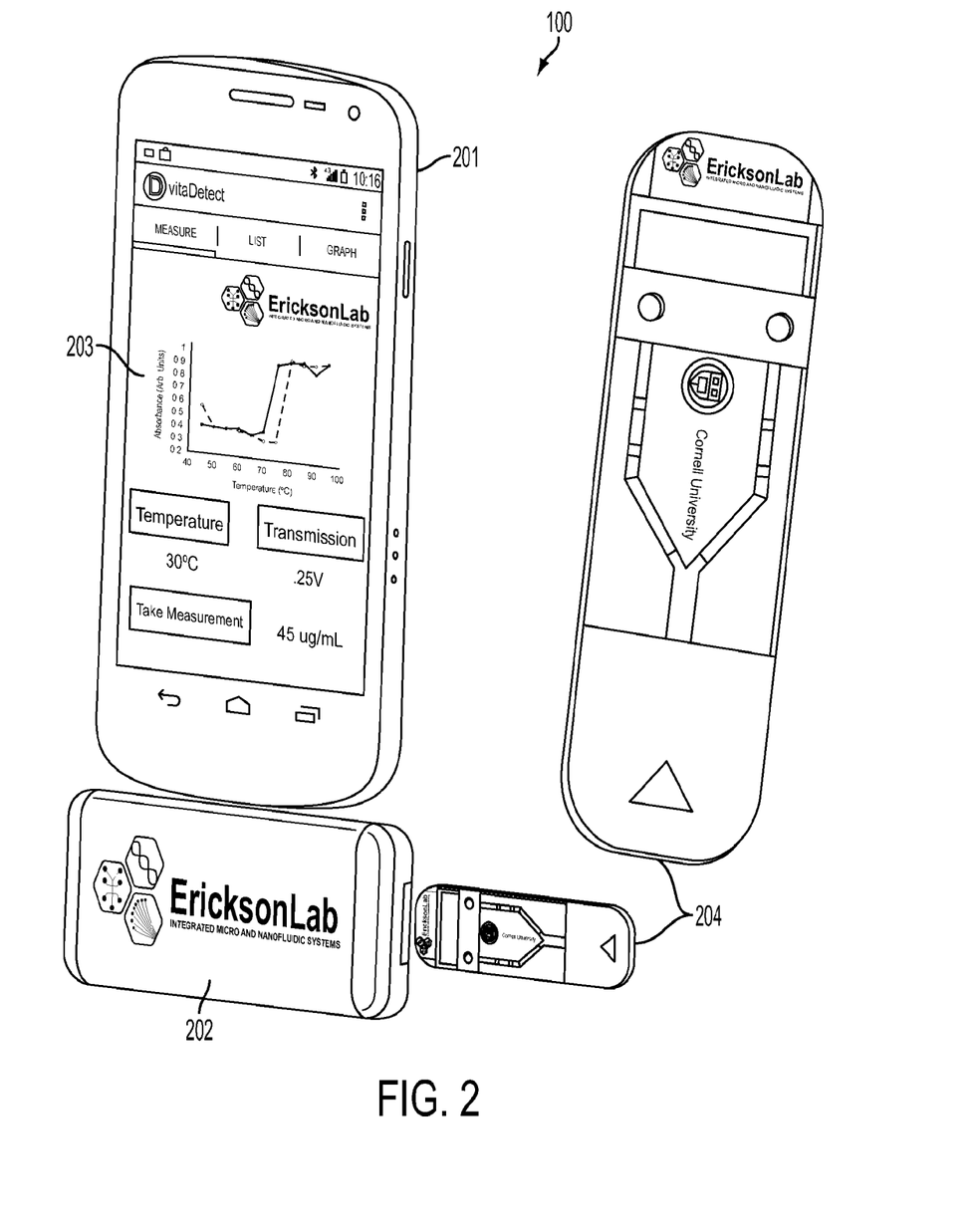
FIG. 2 is a photoreproduction showing a smartphone, a smartphone accessory, and a modular diagnostic test platform with an addition enlarged view of the diagnostic test platform, according to an exemplary, non-limiting embodiment of the invention.
Figure 3:
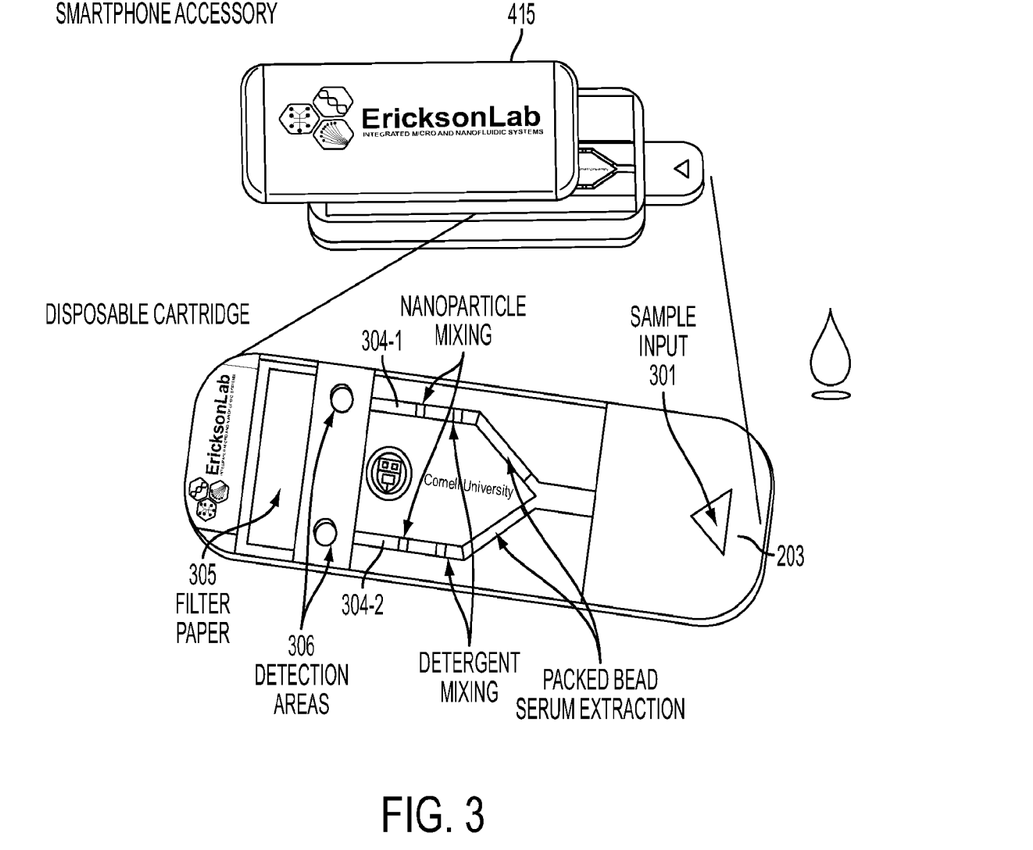
FIG. 3 is a photoreproduction showing the smartphone accessory and the modular diagnostic test platform illustrated in FIG. 2 with the diagnostic test platform inserted in the smartphone accessory.
Figure 4:
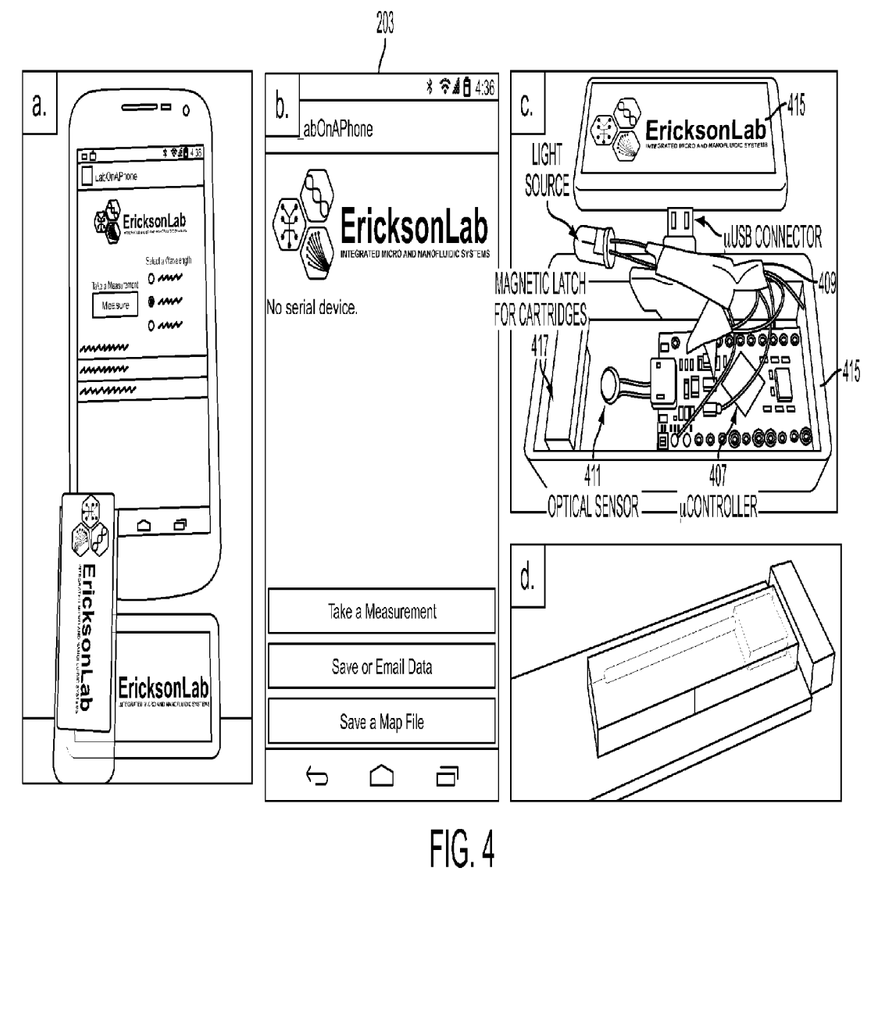
FIG. 4 shows: *a*) a smartphone system as depicted in FIG. 2; (*b*) a smartphone app user interface; (*c*) components of a smartphone accessory as depicted in FIG. 2; and, (*d*) a disposable modular diagnostic test platform, according to an exemplary, illustrative embodiment of the invention.

An exemplary smartphone system 100 is shown in FIGS. 2 and 4 and includes a smart phone component 201, a smartphone accessory component 202, and a smartphone software application 203 (illustrated by a user interface display). Also shown in FIGS. 2 and 3 is an illustrative embodiment of a modular diagnostic test platform 204 designed to operate with the smartphone system, and which forms a part of the embodied invention.

Figure 8:
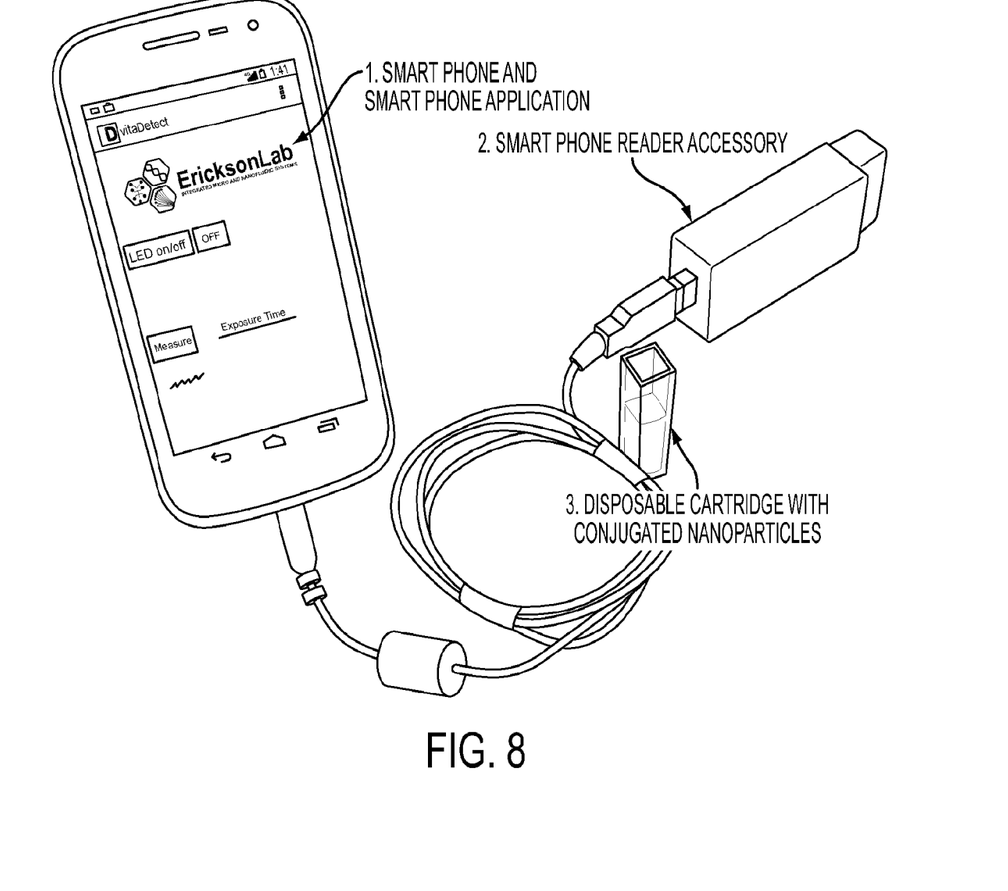
FIG. 8 illustrates a mode of connection between a smartphone and a smartphone accessory according to an illustrative aspect of the invention.

The smartphone component has been described herein above and needs no further description to be well understood. The smartphone accessory 202 connects to the smartphone 201 via USB (as illustrated in FIG. 8), Bluetooth, Wi-Fi, or other supported connection and acts as an interface between the computational power, display, and connectivity of the smartphone along with the biological interface of the modular diagnostic test platform 204. As a bridge between the two components, the smartphone accessory contains a microcontroller 407 (e.g., an 8 MHz Pro Micro Arduino; FIG. 4) or equivalent component capable of communicating with the smartphone and capable of controlling any number of actuators, signal transducers, or other components. In an exemplary aspect further illustrated in FIG. 4, the smartphone accessory contains an LED 409 or other light source and a photodiode, photocell, or other optical transducer 411, which with some additional optical components that are not part of the invention per se functions as a smartphone-based spectrometer. In alternative aspects, the smartphone accessory could contain a laser, a spectrometer, and/or a Raman detector.

As will be described in greater detail below, the light source 409 has a wavelength that corresponds to the absorbance peak of a functionalized nanoparticle reaction (in the examples to follow, functionalized gold nanoparticles (GNPs) are used having a resonant absorbance peak at 520 nm. The microcontroller 407 connects to a male μUSB connector in order to draw power from and communicate with the smartphone. The smartphone accessory 202 is enclosed in a housing 415 to block out ambient light.

As further illustrated in FIG. 4, the housing 415 holds the LED 409 directly across from the photodiode 411, both behind pinhole apertures (not shown). When a modular diagnostic test platform 204 (described in detail below) is inserted into the accessory, the path between the two components is filled with a 1 cm path length fluidic channel full of a nanoparticle solution. An optional magnetic latch 417 for aligning and securing the inserted modular diagnostic test platform 204 is further illustrated.

In an illustrative, exemplary aspect, the microcontroller in the smartphone accessory was programmed to communicate with the smartphone when attached and then wait for a signal to collect data. On receiving a signal, the LED was powered ON for five seconds, and then a measurement of the voltage drop across the photocell was made. The photocell was connected via a pulldown resistor, allowing for measurements of its resistance by comparing the drop in voltage across it to the drop in voltage across the resistor. This resistance drop was then directly correlated to the amount of light on the photocell, or as was done, the absorbance of the solution (on the diagnostic test platform) between the light source and photocell.

Figure 5:
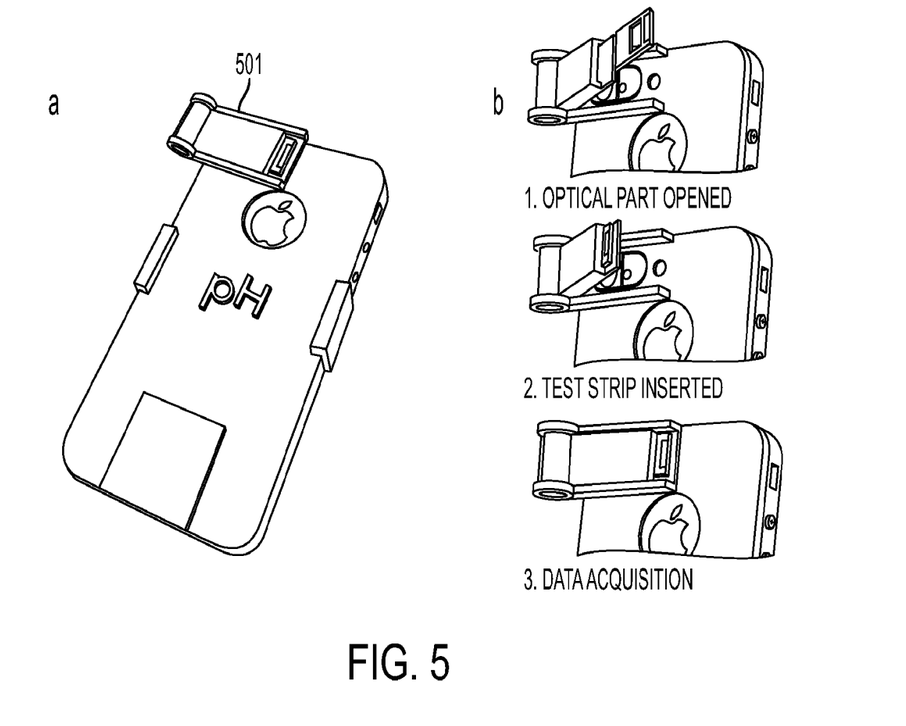

An alternative smartphone accessory 501 is illustrated in FIGS. 5(*a, b*). In this illustrative aspect, the accessory was created integral with a case that attached to the smartphone in such a manner that the smartphone accessory 501 is disposed functionally proximate to a built-in flash component of the smartphone, which, with or without a diffuser/filter, functions as the light source for detection of the target biomolecular reaction. As schematically illustrated in FIG. 5*c* (1, 2, 3), The accessory is opened, the modular diagnostic test platform including the collected sample is inserted therein, and upon closure, a measurement of the biomolecular reaction in the collected sample made and displayed by the smartphone system.

In an illustrative prototype using an Android smartphone platform, a software application 203 was developed in eclipse (REF). The code was written in Java and used the Android SDK tools. The software was written to communicate with a USB accessory in host mode, allowing the Android device to provide power for the smartphone accessory. When triggered via a button press in the application interface (FIG. 4b), a signal is sent to the smartphone accessory requesting a readout of the current absorbance. The application then receives this read-out, displays it to the user, and saves it in a temporary memory. As results are collected, they can also be automatically tagged with user information, time stamps, and locations to provide relevance to the results. In addition to the application's core functionality, utilities were added to email results to other experimenters or medical professionals, to store results as text files on a connected Google Drive account, and to create keyhole mark-up language files (KML files) that could be opened in Google Maps, Google Earth, or many other geographic applications. Using these functions together, a simple database of test read-outs from numerous devices can be created, expanding the applicability of the embodied invention.

An exemplary modular diagnostic test platform 203 (along with the smartphone accessory in which it is designed to operate) is illustrated in FIG. 3. The modular diagnostic test platform, which in the illustrated aspect is disposable, acts as a sample holder and contains all of the necessary components for biomolecular recognition of one or more targets. A sample is collected in a sample input region 301 (e.g., in the case of blood, through a finger-prick similar to a glucose measurement). Biological samples include, but are not limited to, liquids like blood, tears, sweat, urine, or other bodily excretions, as well as solid samples including biopsies. The modular diagnostic test platform includes two microfluidic channels 304-1, 304-2 disposed in parallel. Each contains functionalized nanoparticles and provide structural and functional media (regions) for a biomolecular reaction (304-1) and a control reaction (304-2). In FIG. 3, a filtration region 305 and reaction detection regions 306 are also shown.

Target recognition could be in the form of antibody-antigen binding, DNA base pair matching, aptamer-target binding, enzymatic reaction, or any number of other biological reactions. The reaction could occur on the surface of a substrate, including metal nanostructures for SERS detection, or on a plastic, metal, or other material surface. The reaction could occur between gold nanoparticles for colorimetric, absorption based readouts or between some combination of a substrate and a nanoparticle for other detection methods. The modular diagnostic test platform may contain any form of mechanical, electrical, optical, or other resonators, or other signal transduction technology, to enhance the signal of each biomolecular binding reaction. Diagnostic test platform can be designed to be disposable or washable and reusable.

Prototype microfluidic-based, modular diagnostic test platforms were made of PDMS and glass and plasma-bonded together, as reported in the literature. Briefly, a mold was made from laser cut polyacrylic using a Versa laser. The mold was then cast in PDMS, put under vacuum to removed trapped air bubbles, and baked overnight. The resulting PDMS cast was cut from the mold. One mm of PDMS was retained at the end of the sensing channel, enabling a thin interface for optical measurements along the width of the platform. Holes were punched at the inlet and outlet and the PDMS channels and a microscope slide were then plasma treated in an Oxford Plasma Oxidizer. The treated surfaces were pressed together, and allowed an hour to bond. Fluidic actuation was then provided using a syringe and either annual actuation or a Harvard Apparatus syringe pump.

Figure 7:
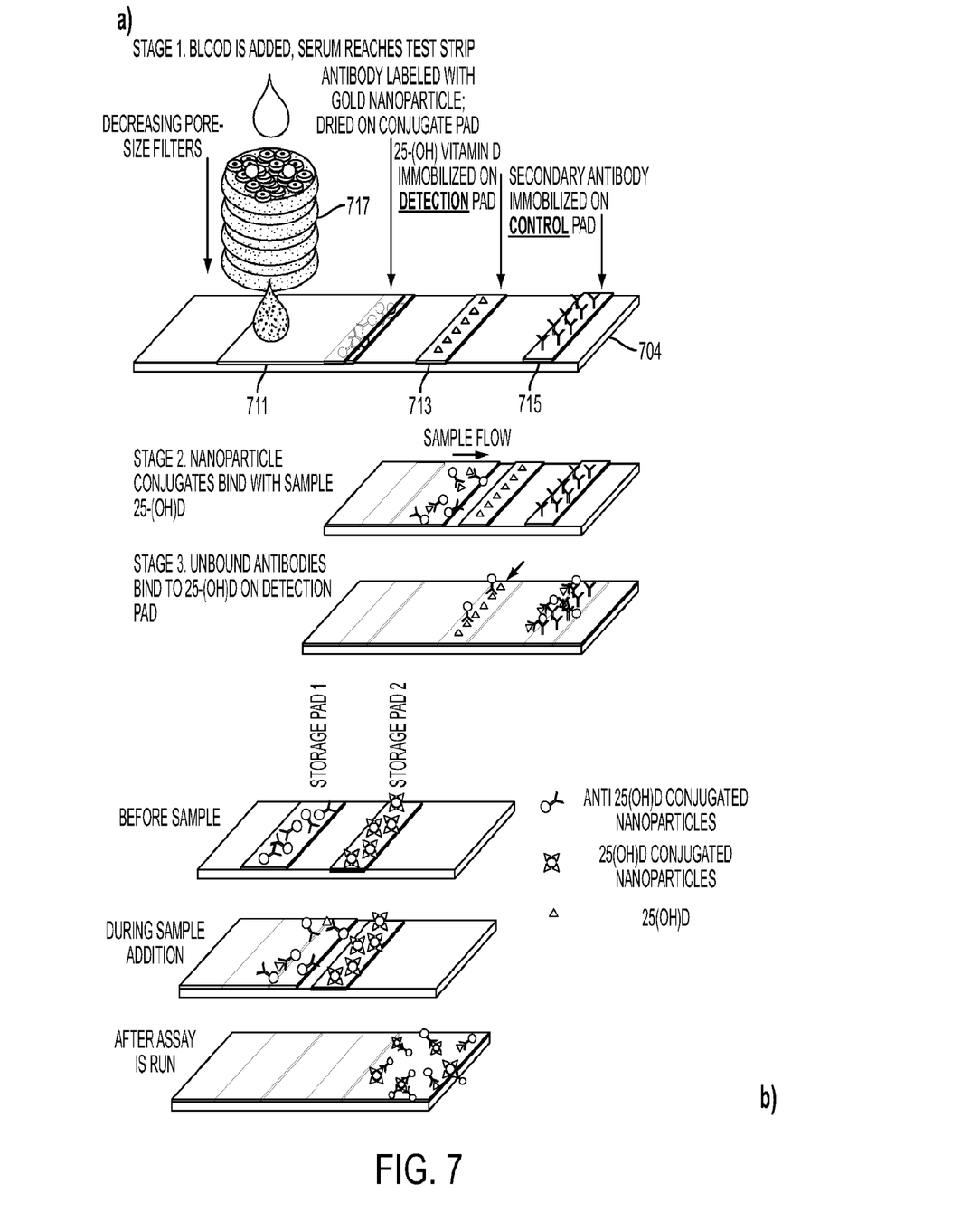
FIG. 7: *a*) schematically illustrates an alternative, exemplary, modular diagnostic test platform (as illustrated in FIG. 6) with details of a competitive Vitamin D assay including blood filtration; *b*) a more detailed view of stages two and three from Fig. (*a*), according to an alternative exemplary aspect of the invention.

An alternative form of a modular diagnostic test platform 704 is schematically illustrated in FIG. 7 (a, b). In this aspect, the sample collection region 711, a biomolecular reaction region 713, and a control reaction region 715 are disposed serially on the platform substrate. A sample filtration component 717 is also illustrated. FIG. 7b further illustrates the stages two and three shown in FIG. 7a.

Exemplary targets that have been measured by the inventors include vitamin D (in the blood) and DNA from Kaposi's sarcoma associated herpesvirus.

Example I

Quantitative Measurement of 25-Hydroxyvitamin D

In this example, a modular diagnostic test platform ("test strip") 704 as shown in FIG. 7 was used. A blood filtration component 717 was incorporated onto the test strip 704 to filter a raw blood sample into a serum sample. The filter component 717 comprised a set of stacked commercial filters (Whatman, Kent, UK) of decreasing pore size filters ranging from approximately 2.7 µm (considered to be about the limit to filter highly deformable red blood cells) to 0.7 µm (small enough to filter platelets). (Note that the filter sizes were not optimized for reproducibility, accuracy, and speed in this work).

Figure 6:
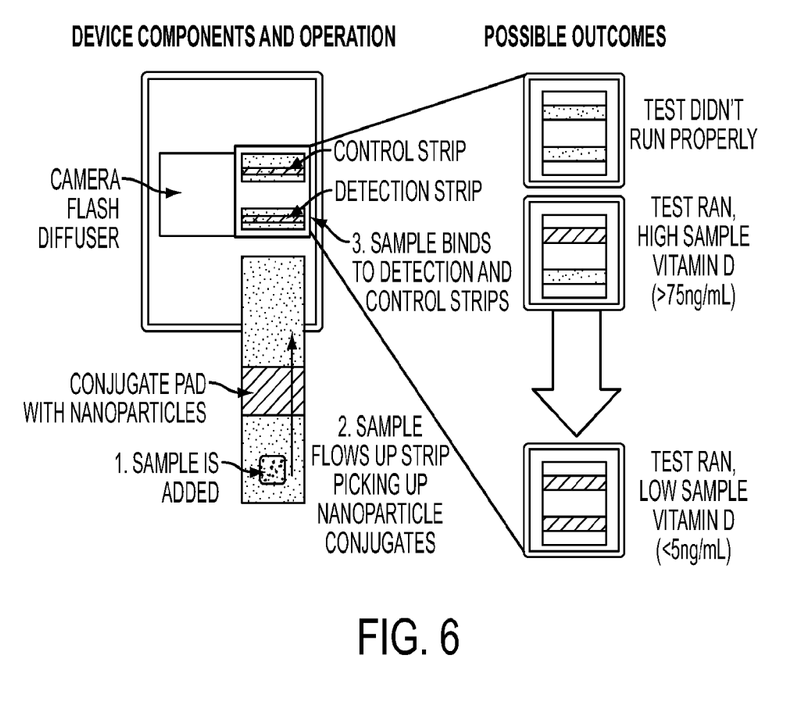
FIG. 6 schematically illustrates an alternative, exemplary, modular diagnostic test platform; (*a*) shows a diagnostic test strip, its components, and its operation; (*b*) illustrates the possible outcomes of running a strip, which are imaged via the smartphone system, according to an exemplary aspect of the invention.

The circulating concentration of 25-hydroxyvitamin D [25(OH)D], a metabolic product of vitamin D, is considered to be the best indicator of vitamin D status. We created a nanoparticle based assay and test strip capable of quantifying 25(OH)D concentration between 5 ng/mL to 75 ng/mL, spanning both the healthy and deficient range. The consumable test strip has a reaction detection region that changes color depending on how much 25(OH)D is present, and a control detection region indicating that the test has run. FIG. 6 shows the test strip, including both the detection and control regions and the upstream conjugation pad with nanoparticles. As shown in detail in FIG. 7, the assay is based around competitive antibody recognition, similar to non-portable vitamin D assay. Instead of using an enzymatic or radioactive label, however, the antibodies are conjugated to 30 nm gold nanoparticles (Nanopartz, Loveland, Colo.). The nanoparticles have a strong red color characteristic of their surface plasmon resonance and high molar absorptivity ($3.25$ $M^{-1}cm^{-1}$). As further shown in FIG. 7 following insertion of the test strip in the accessory, the sample flows downstream (via capillary action) and mixes with 5 µL of 10 nM nanoparticles stored on the surface. Some of the nanoparticle conjugates bind to the 25(OH)D from the sample. The mixture is then transported further downstream over the detection strip, which contains approximately 20 ug/ml of immobilized 25(OH)D. For samples with high vitamin D (e.g., >75 ng/mL), most of the nanoparticle antibodies will end up conjugated to the sample, resulting in only a subtle change in the color of the detection band. For samples with vitamin D between 75 ng/mL and 5 ng/mL, the band will turn redder, allowing for a quantifiable readout of vitamin D levels. Samples with vitamin D under 5 ng/mL saturate the detection band, indicating a severe deficiency. Downstream past the detection region, a control region is functionalized with anti-25(OH)D antibodies. These will bind to passing antibodies indicating the test ran and act as a positive control.

Detection regions of the test strip were prepared by coating a pre-defined quantity of 25(OH)D molecules onto the surface. The passive adsorption used for most antibody immobilization to surface could not be used here to yield stable coatings due the small size of 25(OH)D molecules. Therefore, we used a well-established maleic anhydride to amine chemistry to covalently immobilize 25(OH)D molecules. To do so, coating concentrations of 25(OH) D were enriched with amine functional groups that acted as linkers to the maleic anhydride activated surfaces.

Preliminary vitamin D tests to confirm the functionality of the detection surface and the gold nanoparticle based competitive detection scheme were carried out using a custom-built chamber with wells (not shown). Each well, representing a detection zone, had a 7 mm diameter and corresponded to the well size generally used in commercial 96-well plates. Here, three sets of 10 nM nanoparticle antibodies were mixed separately with samples of high (75 ng/ml), low (5 ng/ml) and zero 25(OH)D concentrations. The mixtures were introduced to the different wells and incubated for four hours. Following washing, silver enhancer solution (Sigma Aldrich) was introduced and the color development after five minutes was observed. The intensity of developed color is proportional to the amount of nanoparticle-antibody conjugates that are bound on the surface. The nanoparticle antibodies that have interacted with the higher concentration of 25(OH)D will have the less antibody conjugates available for binding to the detection surface, which leads to a lower intensity signal in our test.

Procedure for Obtaining Detection Surface

Glass substrate were immersed in 20 mM APTES in isopropanol for two hours and subsequently annealed at 120° C. for one hour. One (1) % PSMA dissolved in toluene was spin-coated at 3500 rpm for 30 s followed by curing at 120° C. for two hours. The glass substrates were then cooled and immersed in acetone for 10 minutes. The 25(OH)D was coated by incubating 20 ug/ml of aminopropylated 25(OH)D at 37° C. in a humid chamber for four hours. The surface was washed and the remaining sites were coated with blocking buffer.

Example II

Detection of Kaposi's Sarcoma Associated Herpes Virus (KSHV) DNA

In this example, a modular diagnostic test platform of the type illustrated as 203 in FIG. 3, and described herein above, was used.

Short DNA sequences used as probes for KSHV DNA were designed using BLAST Primer Design. Briefly, oligo-nucleotides specific to KSHV DNA that code for vCyclin were chosen. Gold nanoparticles were conjugated with oligonucleotides with 5' alkyl thiol groups. The nanoparticles had an average diameter of 15 nm, a compromise between the higher sensitivity of larger particles, and the easier to work with nature and stability of smaller particles. 100 µL of 100 µM KSHV probes were added per 1 mL of 3 nM GNP solution, and allowed to react overnight. Concentrated solutions of sodium phosphate and sodium dodecyl sulphate (SDS) were then added in order to bring the solution to 10 mM and 0.01% concentrations, respectively, before another overnight period to reaction. Next, three additions of sodium chloride were added, resulting in concentration of 100 mM, 200 mM, and 300 mM, each with 24 hours in between. This process worked to maximize the number of bound DNAs per particle, making more stable GNP conjugates. The resulting solution was spun down and resuspended in 0.01% SDS three times to remove unbound oligonucleotides. Sodium phosphate and sodium chloride were then re-added to the final solution, resulting in final concentrations of 10 mM sodium phosphate and 300 mM sodium chloride.

Figure 9:
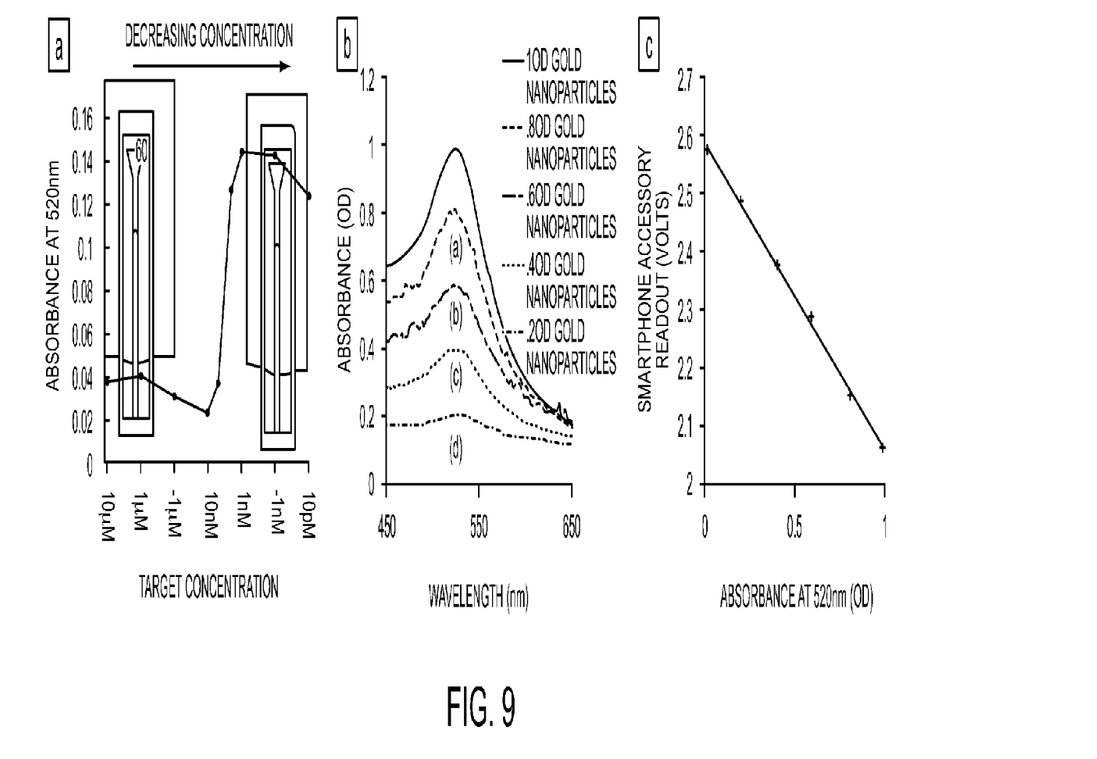
FIG. 9: *a*) (left) Aggregated and (right) unaggregated gold nanoparticle solutions are shown, as well as the absorbance of a solution after the addition of varying amounts of target DNA; *b*) The absorbance spectrums of five different concentrations of gold nanoparticle conjugates; and *c*) The absorbance spectrums of (*b*) used to compare readouts from the smartphone accessory to a spectrometer, according to an illustrative aspect of the invention.

GNP solutions of different concentrations were created in order to calibrate the device. One OD 15 nm GNPs were diluted to concentrations of (a) 0.8 OD, (b) 0.6 OD, (c) 0.4 OD, (d) 0.2 OD, and 0.0 OD. The absorbance of these solutions was measured using a SpectraMAX photometer and the absorbance spectra are shown in FIG. 9b. These solutions were then inserted into the modular diagnostic test platform via syringe, and measured in order to determine the smartphone device read-out at these absorbance levels. By mapping these results to the photometer output, we created a calibration curve for the smartphone accessory.

Next, gold nanoparticle conjugates were mixed with different concentrations of the target KSHV DNA sequence, ranging from 100 µM to 1 µM. After three hours, the solutions were inserted into the smartphone accessory. The solutions were then measured by the smartphone, and the results were saved to a connected Google Drive for analysis.

Gold nanoparticles and their color change can be seen in FIG. 9a after the addition of different amounts of KSHV DNA. For concentrations over 5 nM, a color change reaction was visible. When no target or little target is present, the nanoparticle solution is a bright red. As higher concentrations of target DNA are added, the nanoparticles aggregate, and turn to a duller purple. These color changes can be measured by the smartphone accessory by using a light source tuned to the nanoparticles' absorbance peaks (520 nm) and a photodetector. Further, through changes to the size, shape, and material the nanoparticles, as well as their concentration, the sensitivity of the solutions can be tuned. When the optical density of these solutions is plotted against the absorbance readings taken from the smartphone accessory (FIG. 9c), a strong linear relationship was observed.

In its present configuration, the smartphone accessory had the ability to determine changes in nanoparticle concentration on the order of hundreds of pM. Further, simply by changing the light source and detector, the accessory could be tuned to measure other color change reactions, such as popular enzymatic ones.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

We claim:

1. A method that enables a point-of-collection, quantitative target measurement of a biomolecular reaction in a collected sample, comprising:
   providing a modular, diagnostic test platform that includes a sample collection region, a biomolecular reaction region, and a control reaction region;
   collecting a sample at the sample collection region;
   providing a smartphone and a smartphone accessory,
   wherein the smartphone is programmed with a software application that operatively couples the smartphone and the smartphone accessory,
   further wherein the smartphone accessory is one of operatively connectable to and operatively connected to the smartphone,
   further wherein the smartphone accessory is adapted to removeably retain the modular, diagnostic test platform including the collected sample,
   further wherein the smartphone accessory provides an ambient light-free environment for at least the biomolecular reaction region and the control region of the diagnostic test platform including the collected sample at least during a reaction measurement phase of the method,
   further wherein at least one of the smartphone and the smartphone accessory includes a light source having an emission that can illuminate at least the biomolecular reaction region and the control region of the diagnostic test platform;
   instructing the software application to activate the light source;
   making a plurality of ratiometric measurements at different times, with each ratiometric measurement made of a biomolecular reaction in the biomolecular reaction region and a biomolecular reaction in the control reaction region, thereby producing time-charted measurements; and
   displaying on the smartphone a quantitative target measurement of the biomolecular reaction in the collected sample.

2. The method of claim 1, wherein the biomolecular reaction region and the control reaction region each include a plurality of functionalized nanoparticles.

3. The method of claim 1, wherein the biomolecular reaction region and the control reaction region are in the form of microfluidic channels.

4. The method of claim 3, further comprising making the ratiometric measurement of the biomolecular reaction in the biomolecular reaction region and the biomolecular reaction in the control reaction region in parallel.

5. The method of claim 1, wherein the biomolecular reaction region and the control reaction region are in the form of serially disposed sub-regions on the diagnostic test platform.

6. The method of claim 5, wherein the biomolecular reaction region is disposed upstream of the control reaction region.

7. The method of claim 1, wherein the diagnostic test platform is a single-use, disposable component.

8. The method of claim 1, wherein the smartphone accessory further comprises a microcontroller operatively coupled to the software application, the light source, and a photodetector, wherein the light source emission is at a wavelength that corresponds to a resonant absorbance peak of the pluralities of the functionalized nanoparticles.

9. A smartphone system capable of performing a biomolecular assay on an analyte, comprising:
   a smartphone component;
   a smartphone application component; and
   a smartphone accessory component,
   wherein the components are linked in a manner that enables a quantitative biomolecular assay on an analyte disposed on the diagnostic test platform component,
   further wherein the system is configured in a manner to communicate a quantitative target measurement of the assay and reaction dynamics of the assay; further wherein the reaction dynamics of the assay are configured to be based at least in part on a plurality of ratiometric measurements made at different times during the biomolecular reaction, such that time-charted measurements are produced.

10. The smartphone system of claim 9, wherein the smartphone application component is operatively linked to at least one of a USB-type accessory, a Bluetooth platform, Wi-Fi, and a smartphone input port.

11. The smartphone system of claim 10, wherein the smartphone application component is in a mode such that the smartphone component provides operational power for the smartphone accessory component.

12. The smartphone system of claim 9, wherein the smartphone application component has a user-operated trigger in an application interface that, upon activation, is programmed in a manner to send a signal to the smartphone accessory component requesting a readout of an absorbance value of the analyte.

13. The smartphone system of claim 12, further comprising a data memory structure, wherein the smartphone application component is programmed in a manner to store the readout of the absorbance value in the data memory structure.

14. The smartphone system of claim 11, wherein the smartphone accessory component further comprises:
   a case;
   a microcontroller that is powered by the smartphone component, disposed in the case;
   a light source coupled to the microcontroller, disposed in the case; and
   an optical sensor disposed in a spaced, opposing relation to the light source, disposed in the case,
   further wherein the light source is characterized by an emission wavelength corresponding to a resonant absorbance peak of the nanoparticles.

15. The smartphone system of claim 14, further comprising a modular, diagnostic test platform that includes a sample collection region, a biomolecular reaction region, and a control reaction region.

16. The smartphone system of claim 15, wherein the modular, diagnostic test platform includes a plurality of functionalized nanoparticles characterized by a resonant absorbance peak.

17. The smartphone system of claim 16, wherein the light source emission wavelength corresponds to the resonant absorbance peak.

18. The smartphone system of claim 14, wherein the smartphone accessory component further comprises an optical sensor-respective pinhole aperture disposed adjacent the optical sensor and a light source-respective pinhole aperture disposed adjacent the light source, wherein the respective pinhole apertures are disposed in adjacent, opposing relationship.

19. The smartphone system of claim 15, wherein the diagnostic test platform component is removeably disposed in the smartphone accessory component.

\* \* \* \* \*